US011445741B2

(12) United States Patent
Chanvrier et al.

(10) Patent No.: US 11,445,741 B2
(45) Date of Patent: Sep. 20, 2022

(54) PROCESS FOR SUGAR MODULATION
(71) Applicant: SOCIETE DES PRODUITS NESTLE S.A., Vevey (CH)
(72) Inventors: Helene Michele Jeanne Chanvrier, Orbe (CH); Tram Anh Line Do, Les Hopitaux-Neufs (FR); Jovyn Kye Tyng Frost, Orbe (CH); Dietmar August Gustav Sievert, Saint-Sulpice (CH)
(73) Assignee: Societe des Produits Nestle S.A., Vevey (CH)
( * ) Notice: Subject to any disclaimer, the term of this patent is extended or adjusted under 35 U.S.C. 154(b) by 72 days.
(21) Appl. No.: 16/771,530
(22) PCT Filed: Dec. 7, 2018
(86) PCT No.: PCT/IB2018/059752
§ 371 (c)(1),
(2) Date: Jun. 10, 2020
(87) PCT Pub. No.: WO2019/116183
PCT Pub. Date: Jun. 20, 2019
(65) Prior Publication Data
US 2021/0169111 A1 Jun. 10, 2021
(30) Foreign Application Priority Data Dec. 15, 2017 (EP) .................................... 17207578

(51) Int. Cl.
| A23L 29/30 | (2016.01) |
| C08B 30/18 | (2006.01) |
| C08L 3/02 | (2006.01) |
| C12P 19/22 | (2006.01) |
| C12P 19/12 | (2006.01) |
| A23L 7/104 | (2016.01) |
| B01F 27/70 | (2022.01) |
| C12P 19/04 | (2006.01) |

(Continued)
(52) U.S. Cl.
CPC ............... A23L 29/35 (2016.08); A23L 7/107 (2016.08); B01F 27/70 (2022.01); C08B 30/18 (2013.01);
(Continued)

(58) Field of Classification Search
CPC .. A23L 29/35; A23L 7/107; B01F 7/04; B01F 2215/0014; B01F 27/70; C12P 19/12; A23V 2002/00
(Continued)

(56) References Cited

U.S. PATENT DOCUMENTS

| 3,950,543 A | 4/1976 | Buffa et al. |
| 5,912,031 A | 6/1999 | Fitchett et al. |

(Continued)

FOREIGN PATENT DOCUMENTS

| DE | 2216854 | 10/1973 |
| EP | 0176297 | 9/1985 |

(Continued)

OTHER PUBLICATIONS

Geoffry et al., "Study of the Measurement of Beta Activity and Alpha-Amylase of Wheat Flours", Technical Part, Issue No. 144, Nov.-Dec. 1954, 6 pages.

(Continued)

*Primary Examiner* — Hamid R Badr
(74) *Attorney, Agent, or Firm* — K&L Gates LLP (57) ABSTRACT

The present invention relates to a method for producing a food product comprising hydrolysed starch, as well as to products obtainable by the method. The method has the advantage of increasing the amount of sugar (i.e. maltose) produced by hydrolysis as compared to conventional methods of starch hydrolysis and present the additional advantage of providing good processability for the food product.

20 Claims, 1 Drawing Sheet

(51) Int. Cl.
*C12P 19/14* (2006.01)
*B01F 101/06* (2022.01)

(52) U.S. Cl.
CPC .............. *C08L 3/02* (2013.01); *C12P 19/04* (2013.01); *C12P 19/12* (2013.01); *C12P 19/14* (2013.01); *C12P 19/22* (2013.01); *A23V 2002/00* (2013.01); *B01F 2101/06* (2022.01); *B01F 2215/0472* (2013.01); *B01F 2215/0477* (2013.01)

(58) Field of Classification Search
USPC .......................................................... 426/28
See application file for complete search history.

(56) References Cited

U.S. PATENT DOCUMENTS

| | | | |
|---|---|---|---|
| 2008/0210174 A1 | 9/2008 | Karl et al. | |
| 2009/0005553 A1* | 1/2009 | Hassan | A23L 29/35 536/102 |
| 2011/0020523 A1 | 1/2011 | Pereyra et al. | |
| 2012/0040065 A1* | 2/2012 | Adden | C08B 11/12 426/453 |
| 2012/0040965 A1 | 2/2012 | Adden et al. | |

FOREIGN PATENT DOCUMENTS

| | | |
|---|---|---|
| RU | 2244444 C2 | 1/2005 |
| RU | 2425892 C2 | 8/2011 |
| RU | 2630665 C2 | 9/2017 |
| WO | 03024242 A1 | 3/2003 |
| WO | 2005052148 | 6/2005 |
| WO | 2018011401 | 1/2018 |

OTHER PUBLICATIONS

Russian Office Action for Application No. 2020122599 dated Apr. 11, 2022.

* cited by examiner

PROCESS FOR SUGAR MODULATION

CROSS REFERENCE TO RELATED APPLICATIONS

The present application is a National Stage of International Application No. PCT/IB2018/059752, filed on Dec. 7, 2018, which claims priority to European Patent Application No. 17207578.0, filed on Dec. 15, 2017, the entire contents of which are being incorporated herein by reference

TECHNICAL FIELD OF THE INVENTION

The present invention relates to a method of preparing a food product comprising hydrolysed starch. In particular, the present invention relates to a method of preparing a food product comprising hydrolysed starch with higher amounts of maltose, as compared to conventional hydrolysis processes. The method of present invention also present the benefit of providing good processability for the food product.

BACKGROUND OF THE INVENTION

There is a growing concern of the effects of sugar levels, in particular sucrose levels, in food products, and therefore lower levels of this sugar are often desired. Sugar levels are a particularly important concern in the production of food products for infants and/or children and in some countries, for regulatory reasons, the addition of sucrose is completely banned.

Elimination of crystalline sucrose has a significant impact on processability [of roller-dried cereals] as it leads to a lower film thermoplasticity and therefore affects roller-drying outputs. Compensation of loss of thermoplasticity is a challenge and one possible solution is to increase generation of maltose from the hydrolysis of flour, to maintain similar roller-drying performances.

In current manufacturing processes for production of starch-containing food products, amylolytic enzymes are used to break down starch and decrease product viscosity. High viscosity products are difficult to handle in the manufacturing line, and therefore the starch is treated with enzymes which results in lower viscosity. Starch degradation also leads to the production of disaccharides, in particular maltose among others.

To maximise maltose generation an off-line hydrolysis process could be implemented but such lines are high in costs.

Hence, a new process for hydrolysis of starch generating increased amounts of maltose as compared to conventional process would be advantageous.

SUMMARY OF THE INVENTION

Thus, it is an object of the present invention to provide a method that solves the above mentioned problems of the prior art concerned with levels of sugar in foods comprising hydrolysed starch. More in particular, it is an object of the present invention to provide a method that provides food product comprising hydrolysed starch with higher amounts of maltose, as compared to conventional hydrolysis processes.

It is also an object of the present invention to provide a method to prepare food product comprising hydrolysed starch with higher amounts of maltose, as compared to conventional hydrolysis processes and which method still results in good processability of the food product during its preparation.

Thus, one aspect of the invention relates to a method for producing a food product comprising hydrolysed starch, said method comprising the steps of:
a) Providing a starting material which comprises both starch and at least one amylolytic enzyme,
b) Providing as ingredients: water, optionally at least one further amylolytic enzyme and optionally one or more other ingredients,
c) Mixing the starting material of step a) and the ingredients of step b)
d) adjusting the temperature of the mixture of step c) to a temperature comprised between 55 and 75 deg C., and
e) simultaneously to step d) subjecting said mixture of step c) to high shear mixing,
f) Incubating the mixture of step e) such that the desired degree of hydrolysis is achieved, thereby obtaining a food product comprising hydrolysed starch.

A further aspect of the invention relates to a food product obtainable or obtained by the methods of the invention.

The present invention will now be described in more detail in the following.

DETAILED DESCRIPTION OF THE INVENTION

Definitions

Prior to discussing the present invention in further details, the following terms and conventions will first be defined:

The term 'degrees C.' or 'deg C.' refers to degrees Celsius.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 1 to 10 (including 1 and 10), from 2 to 8, from 3 to 7, from 1 to 9, from 3.6 to 4.6, from 3.5 to 9.9, and so forth. All references to singular characteristics or limitations of the present invention shall include the corresponding plural characteristic or limitation, and vice versa, unless otherwise specified or clearly implied to the contrary by the context in which the reference, is made.

Within the context of the present invention, the expression "at a temperature ranging from X to Y" has to be intended to indicate any temperature which is comprised between the temperatures X and Y, such temperatures X and Y also being also included in the range, unless specifically indicated.

The term "and/or" used in the context of the "X and/or Y" should be interpreted as "X", or "Y", or "X and Y".

Unless defined otherwise, all technical and scientific terms used herein have the same meaning as commonly understood by one of ordinary skilled in the art.

The term "starch" as used herein refers to the polysaccharide macromolecules used for energy storage by most plants. It consists of a large number of glucose units joined by glycosidic bonds. The two high-molecular weight components of starch are amylose and amylopectin. Starch is found for example in cereals, tubers and legumes. Examples of tubers include potatoes, sweet potatoes, cassava, yams etc. Examples of legumes include beans (such as pinto, red, navy), peas, lentils, chickpeas, peanuts etc. When the term "starch" is used in the context of the present invention, it may indicate starch from one plant origin or a mixture of starches from different plant origins.

The term "cereal" as used herein refers any grass cultivated for the edible components of its grain. Examples of cereal are wheat, rice, maize, barley, rye, oats, buckwheat, millet, quinoa, sorghum et cetera.

The term "food product" as used herein refers to a finished product suitable for human consumption and/or to a intermediate preparation which is meant to deliver a finished product after being subject to additional processing step(s), comprising a heat treatment. Specific non-limiting examples of finished food products are biscuits, wafers, cereals (breakfast and infant), bread, bakery products, pizza, cereal milk drink, baby food and the like. Specific non-limiting examples of preparation which are meant to deliver a finished product after being subject to additional processing steps are batters, doughs, slurries and the like.

Within the context of the present invention, "Infant cereal" products identifies two main categories: complete cereal product which need to be reconstituted in water as they already contain all the necessary nutrients to be delivered with the meal; and standard cereal product which are meant to be reconstituted with milk, infant formula, follow-on formula and/or GUMs.

Within the context of the present invention, the term "all family cereals" identifies compositions containing cereals to be consumed by children and adults. For example, all family cereals are reconstituted in milk (whole or skimmed) and consumed in the format of a porridge.

The term "gelatinization" as used herein refers to the process of swelling and opening of starch granules, where the intermolecular bonds of starch molecules in a starch granule are broken, leading to the binding of water and the irreversible dissolving of the starch granule in water. The determination of the gelatinization temperature is well known to the skilled person, and may be performed by e.g. the Kofler hot stage microscopy (see further Table 1 and notes), or for example by Differential Scanning calorimetry (DSC).

The gelatinizing temperature refers to the temperature (or temperature range) at which a starch gelatinizes. Different species of plants yield starches which may have different gelatinization temperatures, and these are well-known in the art. Gelatinization temperature ranges for some starches, are given below in Table 1 by way of example.

TABLE 1

Typical gelatinization temperatures for some starches

| Starch type | Gelatinization temperature range (° C.)* |
|---|---|
| Wheat | 58-61-64 |
| Rice | 68-74-78 |
| Maize (Corn) | 62-67-72 |
| Potato | 58-63-68 |
| Tapioca | 59-64-69 |
| Waxy maize | 63-68-72 |
| Sorghum | 68-74-78 |

*Determined by Kofler hot stage microscopy (onset- midpoint-end) (Table 8.1 "Starch: Chemistry and Technology", edited by James BeMiller and Roy Whistler, Food Science and Technology International Series, Third edition 2009).

The term "amylolytic enzymes" as used herein refers to any enzyme capable of converting starch into dextrins and sugar (mono- or disaccharides). Examples of amylolytic enzymes include amylases and pullulanase. Examples of amylases include alpha-amylases, beta-amylases, gamma-amylases.

Method of the Invention

In conventional processes for preparing starch-containing foods, the viscosity of the starch presents a problem. In order to avoid viscosity build-up, enzymatic hydrolysis of the starch is often performed which may lead, among others, to the production of maltose. The present invention is based on the surprising finding that implementation of the method of the invention yields a food product comprising hydrolysed starch with higher amounts of maltose, as compared to conventional hydrolysis processes.

Maltose generation is believed to be the result of the action of two types of enzymes, working synergistically: (1) the wheat flour endogenous $\beta$-amylases; directly forming maltose; (2) the added BAN ($\alpha$-amylase); forming dextrins (for the $\beta$-amylases to act on) and maltose in lower amounts. Without wishing to be bound by theory, it is believed that each temperature leads to a different combination of enzyme activity levels (as the enzyme are temperature sensitive), thus determining different balance between activities (1) and (2) above mentioned and consequently different extents of maltose generation.

In the studies conducted by the inventors it was surprisingly found that maltose generation proved to be dependent on the mixing conditions implemented for step e). In particular, it resulted that under high shear mixing conditions the maltose formation may be further increased at a temperature ranging from 55 to 75 deg C. Without wishing to be bound by theory, it is believed that, under high shear, mixing results to be more efficient and the associated temperature distribution within the equipment results to be more homogeneous (narrower temperature curve distribution). The lower maltose levels obtained with high shear mixer (in particular with a ring layer mixer) at a temperature ranging from 55 to 75 deg C. might thus be explained by the narrower temperature distribution within the equipment and the resulting higher fraction of slurry exposed to the temperature 65° C., where maltose seems to be preferentially formed (as shown by the results of Example 4).

In particular, the inventors surprisingly found that with the method of the present invention which operates at a temperature ranging from 55 to 75 deg C. under high shear mixing, higher amounts of maltose are formed.

The inventors also surprisingly found that with the method of the present invention good processability of the slurry which undergoes roller drying process can be obtained. As shown in Example 6 of the present invention the behaviour of the sump obtained according to the method of the present invention was surprisingly bubbly.

"Bubbly" sump in a bi-cylinder roller-dryer is a key processing condition for a good film formation in subsequent roller drying. The bubbling in the sump allows to mix the slurry inside the sump, and prevents the surface from drying up. If the sump does not bubble, then increasing the water content in the slurry is usually required to avoid drying of the surface and issues with roller-drying with a consequent drop of total solids. A drop of total solids is not desired as it leads to output decrease.

The method of the invention thus relates in one embodiment to a method for producing a food product comprising hydrolysed starch, said method comprising the steps of:
- a) Providing a starting material which comprises both starch and at least one amylolytic enzyme,
- b) Providing as ingredients: water, optionally at least one further amylolytic enzyme and optionally one or more other ingredients,
- c) Mixing the starting material of step a) and the ingredients of step b)
- d) adjusting the temperature of the mixture of step c) to a temperature ranging from 55 to 75 deg C., and
- e) simultaneously to step d) Subjecting said mixture of step c) to high shear mixing,
- f) Incubating the mixture of step e) such that the desired degree of hydrolysis is achieved, thereby obtaining a food product with hydrolysed starch.

In one aspect, the method of the invention provides a food product comprising hydrolysed starch which comprises higher amounts of maltose than the food product obtainable via conventional methods not comprising high shear mixing in step e).

Starting Material

The method of the invention involves providing a starting material which comprises both starch and at least one amylolytic enzyme.

Some embodiments relate to methods according to the invention wherein the starting material is a plant preparation, such as a preparation of that part of the plant which contains the majority of the plant's starch storage granules. In some embodiments such preparations may also include other parts of the plant, such as stems, leaves etc. Such plant preparations typically also comprise at least one amylolytic enzyme.

In particular embodiments, the starting material is a dry plant preparation, such as a flour. Thus, the starting material may be selected from a flour of one or more grains, such as a flour selected from wheat flour, rice flour, maize flour, barley flour, rye flour, oat flour, buckwheat flour, millet flour, quinoa flour, sorghum flour; a flour made from one or more tubers, such as potato, cassava; a flour made from legumes such as pea flour; or combinations thereof.

In one embodiment, the starting material comprises at least a portion of wheat flour.

The term dry as used herein means comprising water in the range from 0.01 to 20% w/w such as from 0.01 to 16% w/w, 0.01 to 15% w/w, 0.01 to 12% w/w, 0.01 to 8% w/w, 0.01 to 5% w/w, 0.01 to 3% w/w, w/w such as 0.01 to 0.5% w/w %, or for example being essentially free from water. For example, wheat flour may contain up to 15% moisture (w/w), such as from 12 to 15% w/w, 12 to 14% w/w or 12 to 13% w/w, and is considered a dry plant preparation.

The term flour as used herein refers to the product of milling. The particle size or particle size distribution of the flour is not considered to be critical for the method. Plant preparations in the form of flours which are suitable as starting material for production of hydrolysed starch are known in the art, and selection of such is also within the skill of the person skilled in the art.

Endogenous Amylolytic Enzymes

The starting material for the method of the invention comprises both starch and at least one amylolytic enzymes. The at least one amylolytic enzymes present in the starting material may be endogenous amylolytic enzymes. In other words, the starting material may comprise amylolytic enzymes which have not been added by human intervention, but rather have been co-extracted together with the starch (granules) from the plant material, i.e. endogenous amylolytic enzymes. Examples of endogenous amylolytic enzymes include alpha-amylases, and beta-amylases and gamma amylases. In one embodiment, endogenous amylolytic enzymes are beta-amylases.

The invention in one embodiment relates to a method according to the invention wherein in step d) is the temperature of the mixture of step c) is adjusted to a temperature ranging from 55 to 75 deg C. Such temperature adjustment is simultaneous to subjecting the mixture of step c) to high shear mixing as described in step e).

Providing Water

The method of the invention comprises providing water and mixing with the starting material. Enzymatic hydrolysis of starch requires the presence of water. If the starting material is provided in dry form, such as for example a dry plant preparation, such as for example a plant flour, water may be provided by one or more of steam injection, addition of water, the provision of an aqueous further ingredient, provision of an aqueous solution of at least one further amylolytic enzyme or combinations thereof.

If the starting material is not in dry form, but comprises more than 20% water w/w, or for example more than 15% water w/w, the water may be considered to be at least partially provided by the starting material. In some embodiments, further water may also be provided, for example by one or more of steam injection, addition of water, the provision of an aqueous further ingredient, provision of an aqueous solution of at least one further amylolytic enzyme or combinations thereof.

In particular embodiments, the provision of water comprises providing water in the form of steam. In particular embodiments, water in the form of steam is provided by way of steam injection, such as direct steam injection. In other embodiments, water in the form of steam is provided by way of steam infusion (where ingredients are sprayed in a steam atmosphere). Direct steam injection has the advantage of rapidly heating the mixture of starting material, the optionally water provided from above-mentioned other sources, the at least one further amylolytic enzyme and any optional further ingredients, at the same time as water is added.

Direct steam injection may be achieved by any suitable means, and the selection of such a means is within the skill of a person of ordinary skill in the art.

In one embodiment, when the provision of water is at least partially in the form of steam, such steam provision may occur simultaneously to steps d) and e).

Some embodiments relate to the method according to invention, wherein said mixture (step c) has a total solids content in the range of 20 to 60% w/w, such as 30 to 60% w/w, such as 35 to 60% w/w, such as such as 40 to 60% w/w, such as 45 to 60%, such as 50 to 60% w/w, such as 55 to 60%; or for example from 20 to 55% w/w, 20 to 50% w/w, 20 to 40% w/w; or for example 30 to 50% w/w, or 30 to 40% w/w.

Further Amylolytic Enzymes

The method of the invention comprises a step wherein optionally at least one further amylolytic enzyme is added to the starting material and mixed together with the starting material. Thus, in step b) an amylolytic enzyme may be provided, which is in addition to the amylolytic provided in step a), and all ingredients mixed in step c).

In some embodiments, the at least one further amylolytic enzyme is provided in addition to an endogenous amylolytic enzyme provided in step a).

The at least one further amylolytic enzyme may be any suitable amylolytic enzyme, for example an amylase (such as alpha-amylase and/or beta-amylase) and/or pullalanase. In particular embodiments, the at least one further amylolytic enzyme is one or more of an alpha amylase and a beta amylase. In particular embodiments, the at least one further amylolytic enzyme is one alpha amylase The invention in some embodiments relates to a method according to the invention wherein said at least one further amylolytic enzyme comprises or consists of amylase, for example alpha-amylase not endogenous to the provided starting material.

As mentioned above, the at least one further amylolytic enzyme may be provided as an aqueous solution.

Amylolytic enzymes are commercially available from several distributors, for example from DuPont, Novozymes, DSM, BioCatalysts.

Further Ingredients

In some embodiments of the invention, one or more other ingredients are included. The one or more further ingredients may be any ingredient suitable for a food. In particular embodiments, the one or more other ingredients added in step b) are not negatively affected by the temperature and high shear mixing of step d) and e). Examples of one or more other ingredients may be fats such as oils, protein or amino acid sources, carbohydrate sources such as sugars and/or pre-biotics, minerals, vitamins and the like.

In some embodiments of the method, the food product obtained by a method of the invention is itself a finished food product. In such embodiments, at least one other ingredient is provided in step b), such as one or more ingredients such as for example fats such as oils, protein or amino acid sources, carbohydrate sources such as natural or refined sugars and/or pre-biotics, minerals, fruit ingredients, milk based ingredients and vitamins. In one embodiment, fats such as oils are provided in step b).

Mixing and Premixing

The method of the invention comprises a step of mixing the starting material of step a) and the ingredients of step b).

It is not believed that this mixing is critical, and thus may be done in any suitable manner. The selection of a method of mixing is within the skill of a person skilled in the art.

In some embodiments of the method according to the invention, the step c) of mixing the starting material of step a) and the ingredients of step b), is performed prior to the step d). This means that the starting material and ingredients are mixed prior to the adjustment of temperature which takes place in step d). This is referred to as "pre-mixing".

However, premixing of ingredients is not necessary: dry ingredients and water can be directly fed inside the high shear mixer, such as a Ring Layer Mixer.

In other, particular embodiments, the step c) of mixing takes place simultaneously with step d). For example, the starting material of step a) and the ingredients of step b) may be fed to a container, in which heating is performed and in which, at the same time, mixing takes place. In one embodiment, steps c), d) and e) are performed in a ring layer mixer, simultaneously.

Adjusting Temperature in Step d)

The method of the invention comprises a step d) where the temperature of the mixture obtained in step c) is adjusted to a temperature ranging from 55 to 75 deg C., for example ranging from 60 to 70 deg C. The temperature is adjusted simultaneously with the high shear mixing of the mixture.

In some embodiments, the extent of gelatinization of the starch is above 40% w/w, for example above 50% w/w, for example above 55% w/w.

In particular embodiments, the step d) (adjusting the temperature of the mixture from step c) to a temperature ranging from 55 to 75 deg C., for example from 60 to 70 is performed by direct steam injection.

High Shear Mixing

The method of the invention comprises a step of subjecting the mixture of step c) to high shear mixing, for example by use of a high shear mixer.

The high shear mixing may be for a time period of 0.5 seconds to 10 minutes, such as 1 second to 10 minutes, such as from 1 second to 5 minutes, such as 1 second to 3 minutes, such as 1 second to 120 seconds, such as 1 second to 90 seconds, such as 1 second to 60 seconds.

The high shear mixing may be such that the mixture is homogenized within a time period of 1 second to 10 minutes, such as from 1 second to 5 minutes, such as 1 second to 3 minutes, such as 1 second to 120 seconds, such as 1 second to 90 seconds, such as 1 second to 60 seconds.

In particular embodiments, the high shear mixing is such that the mixture is homogenized within a time period of 1 second to 50 seconds, such as 1 second to 40 seconds, 1 second to 30 seconds.

In this context, homogenized means where the starch granules are swollen and dispersed, preferably uniformly, into the media.

Said high shear mixing is performed simultaneously with the adjusting of the temperature discussed above. As discussed, it is believed that the simultaneous temperature adjustment and high shear mixing work together to give hydrolysis of the starch, while maximising the production of maltose.

Shear forces are unaligned forces pushing one part of the body in one direction, and another part of the body in the opposite direction.

In some embodiments, the invention relates to methods of the invention wherein said high shear mixing in step e) may be achieved by using a high shear mixer. High shear mixers disperse an ingredient or ingredient mix into a main continuous phase, for example a solid, semi-liquid or liquid phase. Typically, a mobile rotor or impeller is used together with a stationary component known as a stator together to create high shear. Thus, a high shear mixer may be defined as a mixer comprising a rotor and at least one stator. Examples of high shear mixers are well known in the art, and include for example ring layer mixers.

Non-limiting examples of high shear mixers according to the present invention are: ring layer mixer, homogenizer, paddle mixer, pin mixer, pelletizer, granulator and high shear pump.

In one embodiment of the present invention, the high shear mixing in step e) is not an extruder. In one embodiment, the high shear mixer according to the present invention is not an extruder.

The term high shear mixing as used herein may be defined as the mixing which achieves such shear as may be achieved by using a Ring Layer Mixer, for example under the conditions described in the Examples.

Ring Layer Mixer

Any apparatus which can achieve high shear mixing as well as allow for simultaneous temperature adjustment may be used.

Particular embodiments of the invention relate to methods according to the invention wherein the high shear mixing step e) is achieved by use of a high shear mixer, in particular a ring layer mixer.

A ring layer mixer delivers high peripheral speeds. The resulting centrifugal force brings the product outwards into a ring layer on the vessel side wall. The high speed difference between the rotating agitator and the mixing drum, combined with the use of different mixing elements ensures a high shear mixing.

Direct steam injection is simple to implement when using a ring layer mixer, which is a further advantage of using a ring layer mixer. This is due to the fact that injection may be carried out at atmospheric pressure.

Some embodiments relate to the method according to the invention, wherein steps c) to e) are performed in a Ring Layer Mixer. Other embodiments relate to where steps c) up to and including at least a part of step f) are performed in a Ring Layer Mixer Particular embodiments relate to methods of the invention wherein the steps a) to e) are performed in a Ring Layer Mixer. As mentioned below, other embodiments relate to methods of the invention wherein steps a to c) are performed prior to use of the ring layer mixer (i.e., pre-mixing step) and steps d) to e) are performed in the ring layer mixer.

Other particular embodiments relate to the method of the invention where direct steam injection is used to adjust the temperature in step d) and ring layer mixer is used for high shear mixing of step e).

In one embodiment of the present invention, the speed of the ring layer mixer may range from 500 to 2500 rpm.

Incubating

The method according to the invention comprises the step f) of incubating the mixture obtained by high shear mixing from step e) such that the desired degree of hydrolysis is achieved.

This incubation step relates to a step when the mixture from step e) is kept at a certain temperature, for a certain period of time. This incubation allows the enzymes, to act in order to hydrolyse the starch. In some embodiments, mixing may take place in the incubation period. The mixing avoids sedimentation, and/or facilitates an even and stable temperature profile. In particular embodiments, the mixing in step f) is not high shear mixing.

In some embodiments, the incubation of step f) is performed at a temperature ranging from 55 to 75 deg C., for example between 60 and 70 deg C.; for a period of time in the range from 1 minute to 24 hours, such as 1 minute to 12 hours, such as from 1 minute to 10 hours, such as from 1 minute to 8 hours, such as 1 minute to 7 hours, such as 1 minute to 6 hours, such as 1 minute to 5 hours, such as 1 minute to 4.5 hrs, such as 1 minute to 4 hours, such as 1 minute to 3.5 hours, such as 1 minute to 3 hours, such as 1 minute to 2.5 hours, such as 1 minute to 120 minutes, such as from 2 minutes to 80 minutes, such as from 10 minutes to 80 minutes, 10 to 60 minutes; or for example from 1 minute to 10 minutes, 1 to 8 minutes, or 1 to 5 minutes, or for example from 2 minutes to 10 minutes.

Further Steps

Yet further embodiments relate to the method according to the invention, further comprising the step g) additional heat treatment of the mixture which was obtained by high shear mixing according to steps a) to f).

The purpose of the heat treatment in step g) is to reduce microbiological load of the product, as well as to inactivate enzymes, including the at least one further amylolytic enzyme from step b). Thus, the temperature and period of time of heat treatment of step g) will be selected in order to fulfil these two requirements and may be performed by any suitable means. It is considered to be within the skill of the person with knowledge in the field to select the means as well as appropriate temperature and time. The heat treatment of step g) may be for example performed by bringing the temperature of the homogenized mixture to a temperature in the range from 90 to 170 degrees Celsius, for a period of time from 2 seconds to 5 minutes.

In particular embodiments, the temperature in step g) is brought to a temperature in the range from 100 to 140 degrees C. for a period of time of 4 seconds to 60 seconds.

In some particular embodiments, the heat treatment of step g) is performed by direct steam injection.

The heat treatment of step g) may be performed after step e), such as directly after step e).

The method of the invention may further comprise one or more further steps wherein one or more yet further ingredients are added to mixture. These ingredients may be any ingredient suitable for the food product being manufactured. In particular, ingredients which are desired to be included in the final food product, but which may be negatively affected by for example the heat and-or the high shear mixing of steps c) and d), may be advantageously added at a point after these said steps. Examples of ingredients which may be negatively affected include heat sensitive nutrients such as heat-sensitive vitamins, and-or probiotics. For example, one or more yet further ingredients may be added after step e), for example after step e) and before step f), or for example immediately after step e), or for example immediately after step e) and before step f). In some embodiments the yet further one or more ingredients may be added after step f), such as immediately after step f) and before any further steps. The person skilled in the art will recognize the requirements of conventional ingredients, including heat-sensitive nutrients and can determine at which point these may be added.

In some embodiments, the method of the invention further comprises a step i) of cooling the mixture obtained by previous step. The cooling may be effected by any suitable means, and may be for example to a temperature in the range from −20 degrees C. to 18 degrees C., such as for example 0 to 10 degrees C., such as 0 to 5 degrees C.

In some embodiments, the method of the invention further comprises steps of drying, for example roller drying, and milling in order to produce a dried product which may be reconstituted before use.

In one embodiment, where optional ingredients are added in step b), the process comprises a drying step j). Drying is defined as the application of heat under controlled conditions, to remove the water present in liquid or semi-liquid foods and to yield solid products.

In one embodiment such step j) is a roller drying step.

The principle of roller drying process (or drum drying) is that a thin film of material is applied to the smooth surface of a continuously rotating, steam heated metal drum. The film of the drying material is continuously scraped off by a stationary knife located opposite to the point of application of the liquid or semi-liquid material. The dryer consists of a single drum or a pair of drums with or without satellite rollers.

Roller drying is a conventional drying technique in the art. The person skilled in the art will be able to select appropriate roller drying temperature and speed for the preparation of food products according to the method of the invention.

In such embodiment, the product obtained may be a finished infant or all family cereal product to be consumed in the format of a porridge after reconstitution as above described.

The Product Obtainable by the Method

The invention relates in a second aspect to a food product obtainable by a method according to the invention. In one embodiment of this aspect, the invention relates to a product obtained by a method according to the invention.

The food product according to the invention may be described as comprising hydrolysed starch and increased amounts of maltose. The term increased amounts of maltose in this context means that amounts of maltose which are increased as compared to amounts maltose produced by conventional starch hydrolysis processes, such as the one described in Example 1. In particular, the amount of maltose is increased as compared to starch hydrolysis methods which do not comprise the steps d) and e) of the present invented method.

In particular embodiments, the invention relates to a product according to the invention wherein the amount of maltose present is increased by up to 100%, for example by 90%, for example by 80%, for example by 70% in comparison to conventional methods for example shown in Example 5 (76%).

In other embodiments, the invention relates to a product according to the invention comprising from 1 to 19%, such as 1 to 15%, or 15 to 19%, or for example 5 to 10% of the amount of maltose present in corresponding product produced by conventional method. In further embodiments, the invention relates to a product comprising more than 9% w/w, such as 9 to 12% w/w, 9 to 19% w/w, or 16 to 30% w/w maltose.

The product of the invention may be a liquid product, comprising hydrolysed starch, or the liquid may be dried. The product may be an ingredient, or a complete food.

In some embodiments of the method, the food product obtained is an intermediate. This means that the food product obtained is itself an ingredient, and as such will be further worked up for example by combining with further ingredients in order to achieve a final food product.

A finished food product means a food product as sold to the consumer. Examples of final food products include infant formulas (e.g. in powder form or ready to drink), cereals, drinks, and the like.

It should be noted that embodiments and features described in the context of one of the aspects of the present invention also apply to the other aspects of the invention.

All patent and non-patent references cited in the present application, are hereby incorporated by reference in their entirety.

The invention will now be described in further details in the following non-limiting examples.

EXAMPLES

Comparative Example 1: Conventional in-Line Hydrolysis Set Up

In this example of a conventional in-line hydrolysis process (where the hydrolysis is performed in the line of production of a finished food product), a wheat flour, water and optionally other ingredients (e.g. sucrose, oils, etc.) are mixed in a preparation tank. The slurry is then pumped into tubes. The alpha-amylase solution is injected in-line; then steam is injected to reach the optimum temperature for the enzyme activity (for example 65 deg C.). The alpha-amylase can also be added in the initial liquid batch preparation tank. The slurry is then further processed at this optimum temperature for a residence time (corresponding to the incubation of step f), depending on the extent of hydrolysis required (e.g. 2 to 10 minutes), before final heat treatment for hygienic reasons and enzymes inactivation (example: above 120° C. for 20 sec). The slurry (comprising around 45% w/w solids) is then subject to a roller drying treatment (heat-treatment step, corresponding to step j) according to the process of the invention) to provide the finished food product which may be then milled and packed for commercial use.

Roller drying treatment is performed in a bi-cylinder roller dryer at a temperature comprised between 150-190 deg C. (for example between 185 and 190 deg C.) and at speed comprised between 0.5 and 5 rpm (for example between 1 and 2 rpm).

Example 2: Method of the Invention in in-Line Hydrolysis

The method of the invention may also be incorporated as an in-line method of hydrolysis in method for producing a finished food product.

In one example of the method according to the invention, the conventional steps of "enzyme dosing—steam injection—incubation" as above described in Example 1 are replaced by a Ring Layer Mixer.

A RLM with 10 litre capacity is used, with speed set between 400 and 3000 rpm (for example between 1500 and 2000 rpm). The RLM has different inlets, wherein the first inlet is used to introduce ingredients' mixture and second inlet for enzyme solution. Steam is injected via the third inlet. The steam is used to bring the temperature of the flour and enzyme mix in the tank to a temperature of 65 degrees Celsius, as measured by a probe. The ingredient mixture is thus heated and homogenized. The resulting treated mixture is transported out of the ring layer mixer to holding tubes. The treated mixture is incubated at 65 degrees C. for a time longer than 1 minutes to allow the further hydrolysis by the enzymes.

The key characteristic of this high shear mixer is that it allows mixing with steam and amylase.

Figure 1:
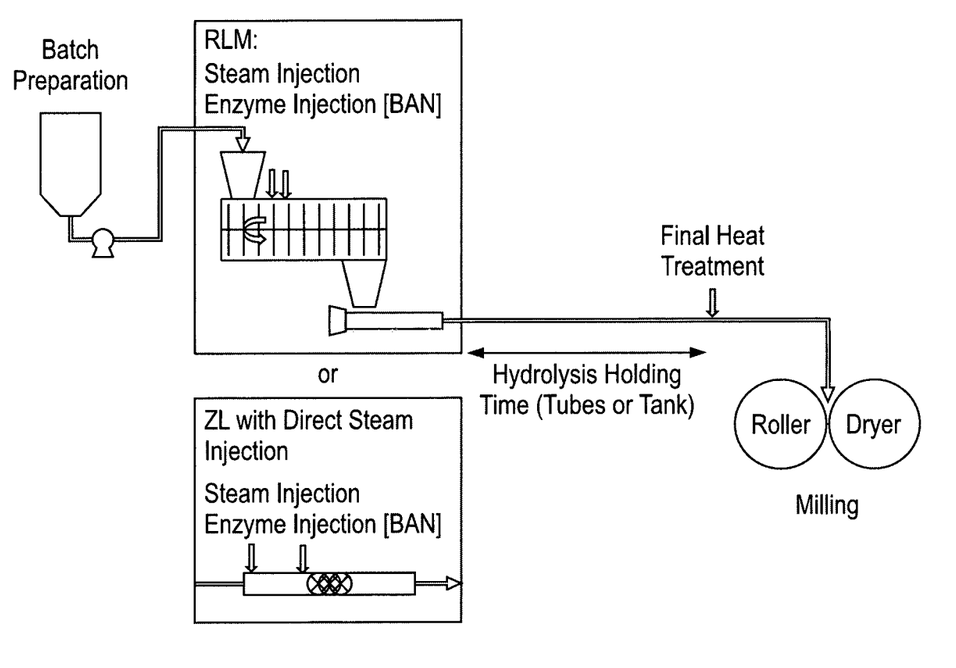
FIG. 1 is a simplified process diagram for the in-line hydrolysis set-up showing equipment according to the process of the invention (Ring Layer mixer—hereby shortened RLM) or conventional equipment (for example a line set up comprising an hydrolysis tank (ZL) equipped with a Direct Steam injector—hereby shortened-DSI).

FIG. 1 is a simplified process diagram for the in-line hydrolysis setup showing equipment according to the process of the invention (Ring Layer mixer—RLM) or conventional equipment (for example a static mixer–ZL).

Comparative Example 3: Conventional in-Line Hydrolysis Set Up Carried Out at Alternative Temperatures With the purpose of comparing the sample with those obtained according to the process of the invention, roller dried cereals samples were prepared as described in Example 1 but operating at a temperature of 40 deg C. or 80 deg C.

Comparative Example 4: In-Line Hydrolysis Set Up Carried Out with Ring Layer Mixer at Alternative Temperatures With the purpose of comparing the sample with those obtained according to the process of the invention, roller dried cereals samples were prepared as described in Example 2 but operating at temperature of 40 or 80 deg C.

Example 5: Comparison of Maltose Content

Maltose reduction was measured in different set ups, with [set-up described in Comparative Examples 1 or 3)] and without ring layer mixer [set up described in Example 2].

Sugars profile (HPAEC method) were analyzed in roller-dried prototypes (obtained analogously as described above in Examples—and are reported in Table 1)

TABLE 1

| | Maltose values | | |
|---|---|---|---|
| | 80° C. | 65° C. | 40° C. |
| ZL (Memil, conventional) | 7.81% (Ex. 3) | 9.25% (Ex. 1) | 4.79% (Ex. 3) |
| RLM | 2.37% (Ex. 4) | 13.5% (Invention) | 2.81% (Ex. 4) |

Table 1 shows that the amount of maltose produced in the set up where a high shear mixer (ring layer mixer) is used along with a temperature of 65 deg C. is drastically increased as compared to that of the conventional (and Ring Layer mixer) set up at all temperatures Example 6: Comparison of Sump Behavior Sump behaviour in a bi-cylinder equipment was investigated for slurries obtained for Examples 1 to 4 as above described before roller drying. The results obtained are reported in Table 2 below:

TABLE 2

| Line set-up | T(° C.) | Bi-cylinder Sump | Max TS (%) | Maltose in cereal powder (containing 75% flour) (g/100 g) |
|---|---|---|---|---|
| ZL (Memil) | 80 | No formation of Vapour Bubbles | 48 | 7.81 |
| | 65 | Bubbly | 50 | 9.25 |
| | 40 | Bubbly | 50 | 4.79 |
| RLM | 80 | No formation of Vapour Bubbles | 48 | 2.37 |
| | 65 | Bubbly | 50 | 13.05 |
| | 40 | Bubbly | 50 | 2.81 |

As above discussed, obtaining a "bubbly" sump in a bi-cylinder roller-dryer is a key processing condition for a good film formation. The bubbling in the sump allows to mix the slurry inside the sump, and prevents the surface from drying up. If the sump does not bubble, then a drop of TS is usually required to avoid drying of the surface and issues with roller-drying. A drop of TS is not desired as it leads to output decrease.

As it results from the results reported in Table 2, the hydrolysis temperature affects the sump "bubbliness". At 80° C., the central sump does not bubble anymore, and the total solids had to be decreased by 2% to enable a proper film formation under the operating conditions under study. A drop of 3% of TS leads to an output decrease of 11%. At 65° C. and below, the sump exhibited bubbles, allowing to maintain the Total Solids (TS) at 50% with a proper film formation and consequent advantage in the output.

As shown by the results reported in Examples 5 and 6, the method of the invention not only allows preparation of food products comprising hydrolized starch that have increased maltose content, but also allows for good processability of the slurry which translate into comparable output to conventional hydrolysis conditions.

The invention claimed is:

1. A method for producing a food product comprising hydrolysed starch, the method comprising:
    a) providing a starting material comprising both starch and at least one amylolytic enzyme;
    b) providing water;
    c) mixing the starting material of step a) and the water of step b) to form a mixture;
    d) adjusting the temperature of the mixture of step c) to a temperature ranging from 55 to 75° C.;
    e) simultaneously to step d), subjecting the mixture of step c) to high shear mixing in a Ring Layer Mixer;
    f) incubating the mixture of step e) such that a desired degree of hydrolysis is achieved; and
    thereby obtaining the food product comprising the hydrolysed starch, wherein the food product comprises increased levels of maltose as compared to those obtainable in a conventional method.

2. The method according to claim 1, wherein in step d) the mixture of step c) is adjusted to a temperature ranging between 60 and 70° C.

3. The method according to claim 1, wherein step d) is performed by direct steam injection.

4. The method according to claim 1, wherein the high shear mixing in step e) is performed such that the mixture is homogenized within a time period of 1 second to 50 seconds.

5. The method according to claim 1, wherein the starting material is a plant preparation.

6. The method according to claim 1, wherein the starting material is selected from the group consisting of a flour of one or more grains, a flour made from one or more tubers, a flour made from legumes, and combinations thereof.

7. The method according to claim 1, wherein the starting material comprises wheat flour.

8. The method according to claim 1, wherein step b) further comprises providing a second amylolytic enzyme of amylase, not endogenous to the starting material.

9. The method according to claim 1, wherein the mixture of step c) has a total solids content in the range of 20% to 60% w/w.

10. The method according to claim 1, the method further comprising:
    g) additional heat treatment of the mixture obtained by the high shear mixing according to steps a) to f).

11. The method according to claim 1, wherein the food product comprises increased levels of maltose as compared to those obtainable in a corresponding method wherein step e) is not performed under high shear mixing.

12. A food product obtainable by the method according to claim 1.

13. The method according to claim 1, wherein the step a) further comprises providing an additional amylolytic enzyme, and the additional amylolytic enzyme is alpha amylase.

14. The method according to claim 1, wherein the food product comprises increased levels of the maltose as compared to those obtainable in a corresponding method wherein step e) is not performed in a high shear mixer.

15. The method according to claim 1, wherein the food product comprises more than 9% w/w of the maltose as compared to those obtainable in a conventional method.

16. The method according to claim 1, wherein the food product comprises more than 16% w/w to more than 30% w/w of the maltose as compared to those obtainable in a conventional method.

17. The method according to claim 1, wherein the speed of the Ring Layer Mixer ranges from 500 rpm to 2500 rpm.

18. The method according to claim 1, wherein the at least one amylolytic enzyme is an endogenous amylolytic enzyme.

19. The method according to claim 18, wherein the endogenous amylolytic enzyme is selected from the group consisting of an alpha-amylase, a beta-amylase and a gamma-amylase.

20. The method according to claim 18, wherein the endogenous amylolytic enzyme is a beta-amylase.

\* \* \* \* \*